United States Patent [19]

Semm

[11] 4,074,719

[45] Feb. 21, 1978

[54] METHOD OF AND DEVICE FOR CAUSING BLOOD COAGULATION

[76] Inventor: Kurt Semm, Hegewischstrasse 4, 23 Kiel 1, Germany

[21] Appl. No.: 699,305

[22] Filed: June 24, 1976

[30] Foreign Application Priority Data

July 12, 1975 Germany .............................. 2531261
Dec. 3, 1975 Germany .............................. 2554336

[51] Int. Cl.² .......................... A61B 17/38; A61N 3/04
[52] U.S. Cl. ............................. 128/303.1; 128/303.17; 219/497; 219/506
[58] Field of Search ........... 128/303.17, 303.1, 303.13, 128/303.14, 303.18, 399; 219/497, 499, 506

[56] References Cited

U.S. PATENT DOCUMENTS

| | | | |
|---|---|---|---|
| 3,234,356 | 2/1966 | Babb | 128/303.14 X |
| 3,527,923 | 9/1970 | O'Neill | 219/497 |
| 3,634,652 | 1/1972 | Shimizu et al. | 128/303.18 X |
| 3,792,231 | 2/1974 | Johnson | 219/497 |
| 3,826,263 | 7/1974 | Cage et al. | 128/303.1 |
| 3,929,137 | 12/1975 | Gonser | 128/303.14 |
| 3,938,526 | 2/1976 | Anderson et al. | 128/303.1 |
| 4,031,898 | 6/1977 | Hiltebrandt et al. | 128/303.1 |

FOREIGN PATENT DOCUMENTS

1,347,865 11/1963 France .............................. 128/303.14
2,360,298 6/1975 Germany ........................... 128/303.17

OTHER PUBLICATIONS

Sugita et al., "Bipolar Coagulator with...Thermocontrol", J. Neurosurg, vol. 41, Dec. 1974, pp. 777-779.

*Primary Examiner*—Robert W. Michell
*Assistant Examiner*—Lee S. Cohen
*Attorney, Agent, or Firm*—Saul Jecies

[57] ABSTRACT

A method and a device for causing blood coagulation are disclosed. Both are especially well suited for use in endoscopy. A support is provided with an end portion on which an electrically operated thermo-element is located which receives electrical current to be heated to a level at which it has a coagulation-causing temperature. A control arrangement maintains the temperature steady when the level is reached. A visual indicator visually shows the heating of the thermo-element to the aforementioned level and an audible indicator audibly indicates the heating of the thermo-element by producing a sound which increases in intensity until the aforementioned temperature level is reached and which thereafter continues at a constant intensity while the temperature is maintained at the aforementioned level.

23 Claims, 8 Drawing Figures

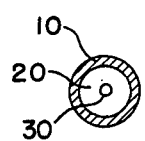
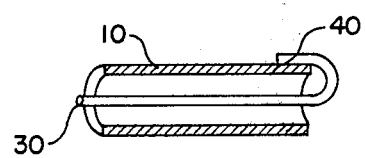
FIG. 3A    FIG. 3B
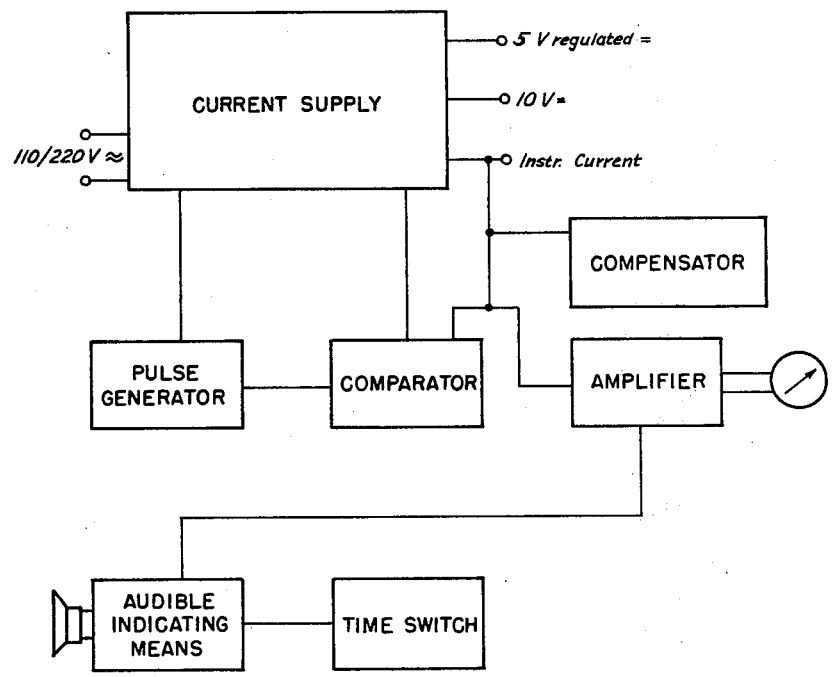
FIG. 2

METHOD OF AND DEVICE FOR CAUSING BLOOD COAGULATION

BACKGROUND OF THE INVENTION

This invention relates to a method of and a device for causing blood coagulation, particularly for use in endoscopy.

In medical applications, such as endoscopy, or hysteroscopy, it is often necessary to be able to cause blood coagulation. From hysteroscopy it is known to provide a probe or pincer which for this purpose is heated to a coagulation-causing temperature which is on the order of substantially 110° to 140° C. However, in the prior art, the instrument is alternately heated and not heated so that a physican using the instrument is forced to observe a temperature-indicating gauge to determine whether the instrument is at the requisite coagulation-causing temperature. This means that he will be distracted from the area where his primary attention should lie, namely from the application of the treatment itself. Moreover, the total coagulation time within which the heating element of the instrument is heated or cooled, is difficult to measure.

Although a suggestion has been made in the prior art to indicate the alternating heating and cooling periods of the device by different signals, this also is not entirely satisfactory because, while the physician is now able to determine whether at any given moment the tool is being heated or is cooling off, he is still somewhat distracted from devoting his entire attention to the treatment he is applying. Moreover, he cannot determine any details of the period during which the tool heats up to the coagulation-causing temperature.

SUMMARY OF THE INVENTION

Accordingly, it is an object of the present invention to overcome the disadvantages of the prior art.

More particularly, it is an object of the invention to provide an improved method of and device for causing blood coagulation, particularly for use in endoscopy, that are not possessed of the disadvantages of the prior art.

In keeping with these objects, and with still other ones that will become apparent hereafter, a feature of the invention resides in a method of operating a blood-coagulating device, particularly in endoscopy, which comprises electrically heating a thermo-element which is mounted on a support and is to supply heat to tissue when its temperature reaches a predetermined level. The heat of the thermo-element is maintained steady when the temperature is reached. The increasing heating-up of the thermo-element to the aforementioned temperature is visually indicated, and an audible indication is provided for indicating the increasing heating-up by generating a sound which increases in intensity until the aforementioned temperature is reached and which thereafter remains steady as long as the temperature itself remains steady.

A device according to the present invention may comprise, briefly stated, a support having an end portion, an electrically operated thermo-element on the end portion, and current supplying means for supplying electrical current to the thermo-element to a level at which it has a coagulation-causing temperature. Control means are provided for maintaining the temperature steady when the level is reached. Visual indicating means visually indicate the heating of the thermo-element to the aforementioned level, and audible indicating means audibly indicate the heating of the thermo-element by producing a sound which increases in intensity until the level is reached and thereafter continues at constant intensity.

The time from the moment at which heating begins until the completion of the heating, i.e. the end of the period for which the predetermined coagulation temperature is required, can be pre-selected and automatically controlled via a timer or time switch. The device may be either in form of a probe or of a pincer. The present invention makes it possible for the treating physician to determine from the increasing intensity level of the sound how the device is heating up and how long the time of the actual coagulation is. If, for example, he is coagulating blood on the tissues of an ovary which he is treating, he can concentrate his full attention on the treating process and need not pay more than minimal attention to the operation of the device in question.

The invention will hereafter be described on hand of exemplary embodiments. The description should be read in conjunction with the appended drawings. However, it should be understood that the description and drawings are exemplary only and that the scope of the protection sought is determined only by the appended claims.

BRIEF DESCRIPTION OF THE DRAWING

FIG. 2 is a block diagram of a circuit according to a further embodiment of the invention;

FIGS. 3A and 3B are respectively transverse and axial cross-sections through a thermo-element used in FIGS. 2 and 3;

DESCRIPTION OF THE PREFERRED EMBODIMENTS

Figure 1:
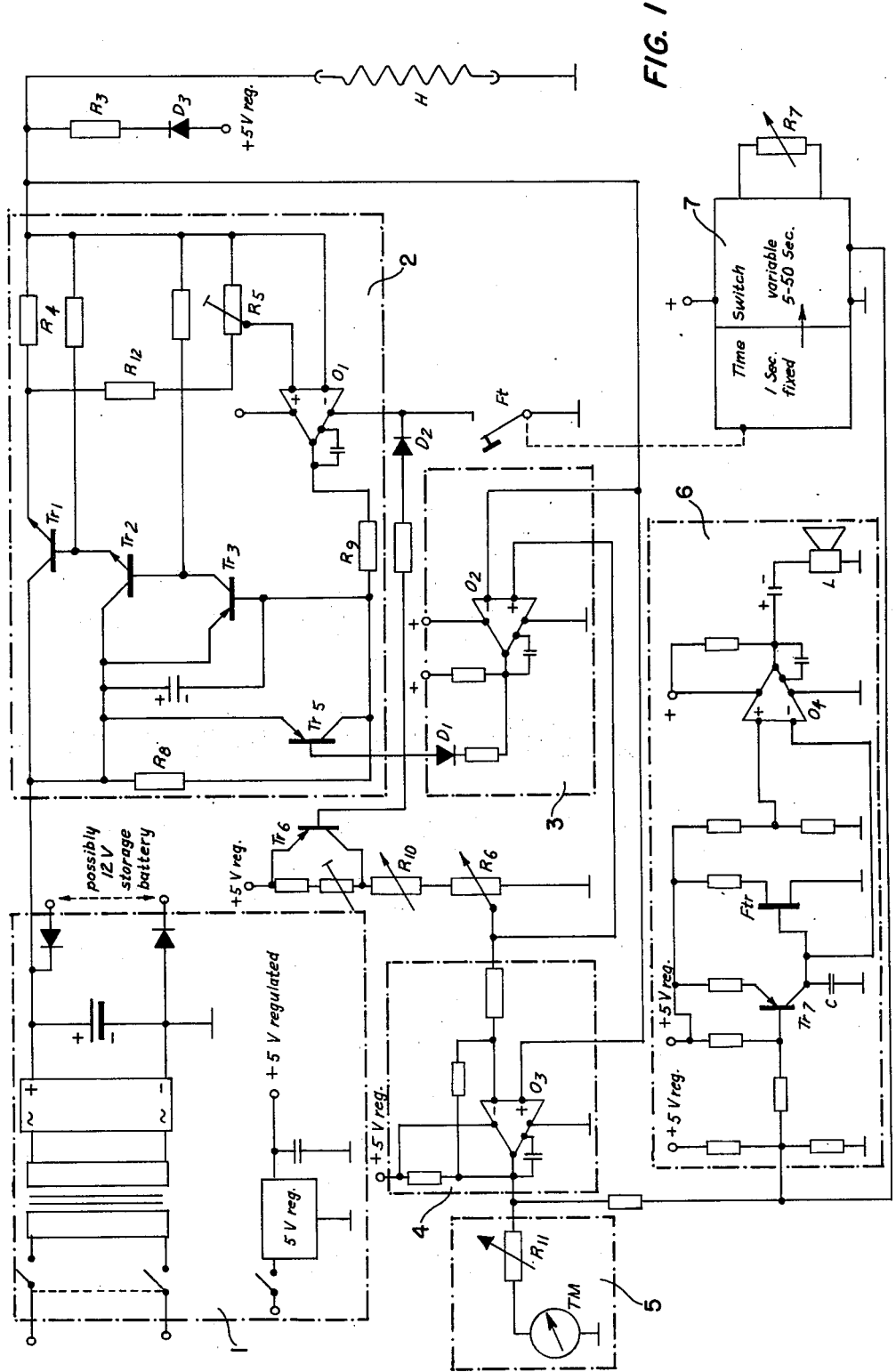
FIG. 1 is a circuit diagram illustrating the electrical circuit of a device according to a first embodiment of the invention.

Referring firstly to the embodiment of FIG. 1 which illustrates a device according to the invention which is heated with direct current it is emphasized that the increase in temperature of the heating element of the device is indicated audibly by a sound which increases in intensity, i.e. which is of increasing frequency, and which changes to a constant frequency and intensity when the selected coagulation temperature has been reached.

The circuit of the device according to FIG. 1 embodies a highly sensitive temperature and current regulating arrangement which maintains temperature and current regulation constant. The circuit in FIG. 1 has a current supply section 1, a current regulating section 2 maintaining the current constant, a temperature regulating section 3, a measuring amplifier section 4, an optical or visual indicating section 5, an acoustic or audible indicating section 6 and a time switch 7.

A heating element H is provided which is heated from a voltage source (+ 5 volts controlled) via a diode $D_3$ and a resistor $R_3$. The heating element H has a positive temperature coefficient and receives an additional current from the section 2, which hereafter for purposes of simplicity will be called the current controller. The current from the section 2 is derived from the emitter of a current amplifying transistor $Tr_1$ and is fed via a resistor $R_4$ to the current supply point E. Two further resistors $R_5$ and $R_{12}$ are connected in parallel to the resistor $R_4$; of these, the resistor $R_5$ is a variable resistor and its tap is connected at the input side of the operational amplifier $O_1$ to the positive pole. The negative pole is connected with the current supply point E. The additional heating current for the heating element H can be selected in accordance with a desired coagulation temperature, by means of the resistor $R_5$, the operational amplifier $O_1$, the resistors $R_8$ and $R_9$ which are of identical electrical values, the transistor $Tr_3$, $Tr_2$ and $Tr_1$. The voltage at the current supply point E is made constant in that more or less additional heating current is fed into the heating element H, so that the total current in the heating element H remains constant. This in turn means that the voltage at the current supply point E and thus the heating output of the heating element H also are maintained constant.

The temperature regulation is effected by the temperature regulating section 3. The tap of a variable resistor $R_6$ is connected with its minus pole to the input of the operational amplifier $O_2$ and the resistor is in turn connected via several additional resistors on the one hand to the positive pole of a controlled 5 volt current source and on the other hand to ground. Connected to the negative pole of the operational amplifier $O_2$ is the voltage at the current supply point E, which voltage is to be maintained constant. The output of the operational amplifier $O_2$ is supplied via a resistor and a diode $D_1$ to the base of the transistor $Tr_5$. The emitter and the collector of the transistor $Tr_5$ are connected in parallel to the resistor $R_8$.

It will be understood that if the voltage at the negative pole and the positive pole of the operational amplifier $O_2$ are equal, no current will flow through the diode $D_1$. If, however, the voltage difference at the positive and negative poles increases that is if the voltage applied to the current supply point E increases, then an additional current is fed to the preheated heating element H until the voltage at the point E again has reached the temperature value which is preseleced with the resistor $R_6$.

The tap of the resistor $R_6$ is connected via a resistor with the negative pole of the operational amplifier $O_3$ which is present in the amplifier section 4. The positive pole on the other hand is connected with the negative pole of the operational amplifier $O_2$ and with the current supply point E. The output of the amplifier section 4 is supplied to the temperature indicating instrument TM and in addition is supplied to the input of the audible indicating section 6.

The audible indicating section 6 comprises in its circuit a saw-tooth wave generator having a transistor $Tr_7$ and a capacitor C as well as a double-base transistor $F_{tr}$. Together with the following circuit and with the operational amplifier $O_4$ it rounds off the teeth of the saw-tooth waves. The thus obtained voltage is supplied via a double capacitor to a loudspeaker L.

When the voltage at the supply point E rises until the constant regulated voltage is reached, this has—at the input to the audible indicating section 6— the result that the saw-tooth wave generator is so tuned that in accordance with the temperature increase until the predetermined constant temperature is reached at the heating element H, it passes from lower to higher frequency, whereas at constant temperature the highest frequency is maintained unchanged. These frequency changes are audible in the speaker L.

Thus, the variable resistor $R_5$ permits the magnitude of heating for the heating element H to be preselected (the heating capacity $J^2 \cdot R_h$, wherein J is the total current in the heating element H and $R_h$ is the resistance of the heating element H). The variable resistor $R_6$ permits the temperature for a constant heating output to be selected. Resistors $R_{11}$ and $R_{10}$ serve to calibrate and set the temperature indicating instrument TM which provides a visual indication.

The heating element H itself is usually made of chrome nickel wire with a high positive temperature coefficient. Particularly suited for this purpose is a wire used conventionally in many applications for thermoelements and known under the tradename of Alumel (TM) which has a particularly high negative temperature coefficient. Alumel (TM) is made by the Phillips Company of the Netherlands and is a miniature thermo-coaxial cable of the type 1 BAC110, having a conductor of a negative thermoelement material Alumel. If the coaxial cable has a 1 mm. outer diameter, its resistance is 3.34 Ohm per meter at an operating temperature of 20° C.

The device according to the present invention is switched on by the treating physician by stepping onto a footswitch, after the electrical switch for the circuit of the current supply section 1 is switched on. The temperature of the heating element H rises to the preselected temperature level and the temperature controller 3 maintains this temperature constant by maintaining constant the current to the heating element H. During heating-up of the element H to the preselected operating temperature, the audible sound issuing from the loudspeaker L rises from a lower to a higher frequency and, when the preselected temperature is reached, the sound remains at the highest frequency reached at that time and is constant until the footswitch $F_t$ is opened again by the treating physician. This means that after closing the footswitch $F_t$ the treating physician can supervise the temperature developments relating to the heating element H merely by listening without having to pay any other attention, and he can interrupt the operation of the device after the heat from the heating element has acted for a period required to effect the desired coagulation.

In order to eliminate even the necessity for having to supervise the coagulation time, the device in FIG. 1 proposes that when the footswitch $F_t$ is closed, a triggering pulse is supplied via a transistor $Tr_6$, a resistor, a diode $D_2$, a broken-line circuit and to a time switch 7 which is thereby triggered. The time switch 7 is composed of two monostable multivibrators which become sequentially operative. The first monostable multivibrator triggers, one second after it has itself been triggered, the second monostable multivibrator (which can be set for a time period of 5–50 seconds via an adjustable resistor $R_7$) and after expiration of the preselected time the second monostable multivibrator shorts out the input of the audible indicating section 6, interrupting the sound issuing from the loudspeaker L and thus telling the treating physician that he must open the footswitch $F_t$.

A further embodiment of the invention is illustrated in FIGS. 2, 3, 3A and 3B. In this embodiment the heating element is heated with direct current in very small steps. In the pause between the steps the thermocurrent which is yielded by the heated heating element that is of a special construction, as will be described later, is measured and thereby the temperature is indicated. Again, the heating is audibly supervised by generation of a sound of varying intensity.

Figure 3:
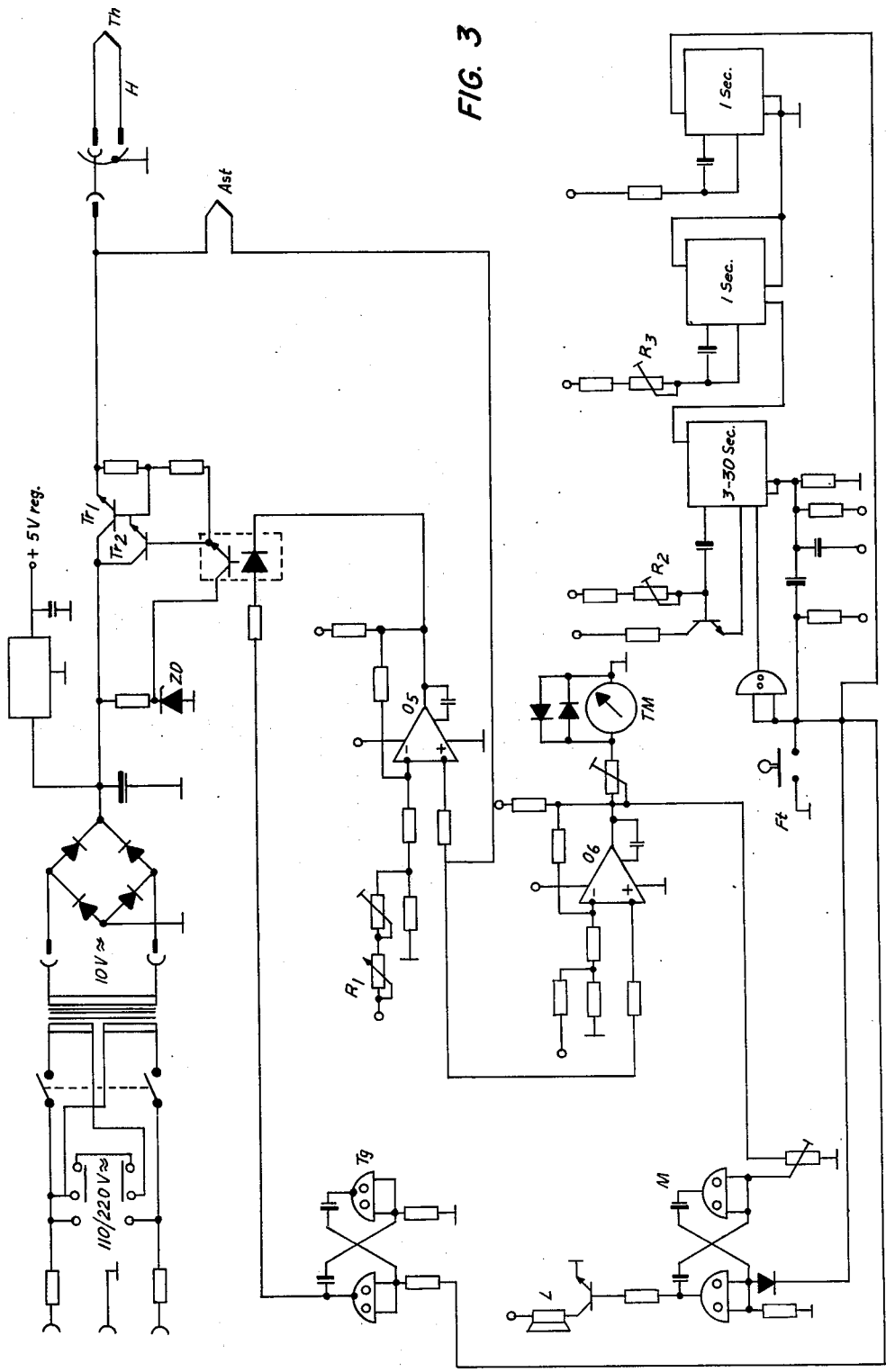
FIG. 3 illustrates the circuit diagram corresponding to the block diagram in FIG. 2.

Before discussing the circuit in FIGS. 2 and 3 in detail, the heating element used in conjunction with this circuit (and illustrated in FIGS. 3A and 3B) will be discussed. This heating element is also produced by the Phillips Company of Holland, and is inherently intended for heating of various media by heat radiation. It is commercially available under the tradename Thermo-Coax (TM) and has a core 30 composed of a chromenickel alloy and a jacket 10 of a stainless steel alloy. The core 30 is embedded in insulating material. If the jacket 10 and the core 30 are welded together at one end, as indicated at point 40 in FIG. 3B, a thermo-element is obtained which with increasing temperature produces an increasing thermal current. The core 30 and the jacket 10 are separated by the insulation 20 as shown in FIG. 3A. Such a thermo element has the advantage that it can be subjected to high current at relatively small core diameter and can carry a relatively high thermal voltage which depends only upon the temperature which prevails at the weld 40, i.e. which is independent of the length of the thermal conductor. Thus, a thermo-element of the type shown in FIGS. 3A and 3B is particularly well suited for such instruments as coagulation probes which have a very small diameter and only a limited length.

The thermo or heating element in FIGS. 3A and 3B is used in the circuit shown in FIGS. 2 and 3. This circuit is the following. A pulse generator M in form of an astable multivibrator is triggered when the footswitch $F_t$ is operated and at the same time a time switch which is composed of a series of monostable multivibrators (3—30 seconds, time adjustable with variable resistor $R_2$; 1 second, time adjustable with variable resistor $R_3$; and 1 second, time fixed) and at the same time a pulse generator $T_g$ is also triggered with a pulse. The astable multivibrator M serves together with a loudspeaker L as a sound generator of the audible indicating means, i.e. the audible indicating section. The pulse generator $T_g$ provides a positive pulse to a so-called opto-coupler, which is a combination of a photoelectric diode with a transistor and which acts in such a manner that when positive voltages of identical magnitude are applied at both sides of the photoelectric diode, the transistor will have no emitter current. In the case of differential positive voltages at both sides of the photoelectric diode, the emitter current of the transistor rises and thus the transistors $Tr_{12}$ and $Tr_1$ amplify this current. The emitter current of the transistor $Tr_1$ is the heating current for the heating element H having the thermo-element $T_h$ (FIGS. 3A and 3B) at its end. The collector of the transistor forming part of the optocoupler is supplied with direct current which is additionally stabilized with a Zener diode ZD.

The positive voltage of the heating element H is supplied via a compensator $A_{st}$ (composed of a thermoelement having the temperature prevailing in the interior of the device) to the positive pole of the operational amplifier $O_5$, which regulates the temperature of the heating element H with the thermo-element $T_h$ as follows: for selecting the temperature there is provided a variable resistor $R_1$ which selects the magnitude of the voltage at the negative pole of the operational amplifier $O_5$. When the voltage at the positive pole of the operational amplifier $O_5$ is greater than the voltage at the negative pole thereof, then the heating element H is heated until such time as the output voltage of the operational amplifier $O_5$ reaches the magnitude of the positive pulse of the pulse generator $T_g$, and thereupon no further heating current flows.

The heating element H is heated only as long as a positive pulse is furnished by the pulse generator $T_g$. The heating element with its thermo-element $T_h$ is thus heated in very small and very rapidly succeeding steps or increments. In the pauses between the positive pulses supplied by the pulse generator $T_g$ the thermo-element $T_h$ supplies a thermal current (depending upon its heating by the heating element H) via the compensator $A_{st}$ to the positive pole of the operational amplifier $O_6$ in the measuring amplifier section. The instrument TM at the output of the operational amplifier $O_6$ shows the respective temperature of the heating element H. The voltage at the measuring instrument TM further influences the activated multivibrator M which serves as the sound generator in the acoustical or audible indicating section 6 via a variable resistor, thus varying its frequency. The variable resistor permits the sound frequency to be preselected and the sound in the loudspeaker L increases with the increase in temperature of the heating element H and in accordance with the increasing thermal current. The sound is immediately interrupted, as is the heating operation, when the footswitch $F_t$ is switched off, or after the preselected time set with the time switch has expired. The output of the monostable multivibrator (1 second fixed) then blocks the astable multivibrator M and the pulse generator $T_g$ is deactivated.

It is clear that with the embodiment in FIGS. 2 and 3, as well as with the embodiment in FIG. 1, the treating physician can interrupt the coagulation treatment at any time, or else the time switch interrupts the coagulation treatment automatically after expiration of a preselected time. In both cases, the audible sound will also be interrupted. Thus, the treating physician receives an audible indication concerning the temperature variations throughout the coagulating operation. He need not observe the temperature measuring instrument and can concentrate fully upon the coagulation of the tissues to be treated.

In many instances it will also be advantageous if the physician receives a further indication, namely if the cooling phase of the heating element is also indicated to him. This may be in form of a sound which decreases in intensity as the heating element is switched off and begins to cool down from the predetermined coagulating temperature. This is particularly desirable in conjunction with a further feature, namely that it be possible to preselect the heating level at which during heating-up of the heating element H the sound of increasing intensity begins, and even more importantly that it be possible to select the heating level at which during the cooling phase the sound of decreasing intensity will cease entirely. The latter feature is especially important because the interruption of the sound of decreasing intensity at a preselected temperature of e.g. 40° or 50° C, furnishes the treating physician with a signal that the coagulationcausing instrument is to be removed from the coagulated tissues. This assures that the coagulated tissues, which have been heated to a temperature of up to 120° C, will not immediately come in contact with not-heated tissues (since the coagulated tissues may be located within the pincers) so that the non treated tissues will not be disadvantageously influenced.

Figure 4:
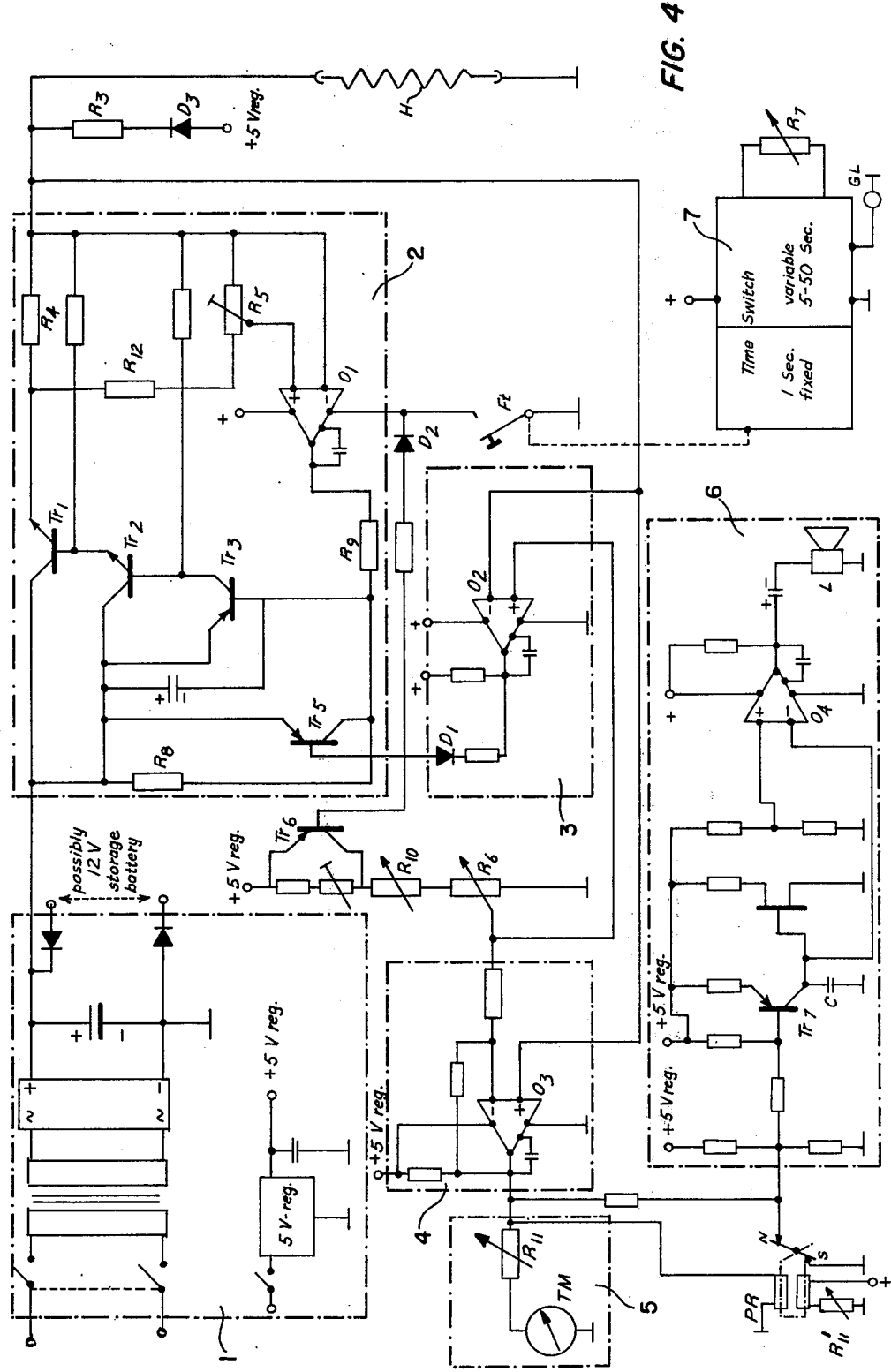
FIG. 4 is a diagram somewhat similar to that in FIG. 1, but illustrating an additional embodiment of the invention.

An embodiment meeting the aforementioned requirements is illustrated in FIG. 4, which shows the circuit of a device of such an embodiment. This circuit essentially corresponds to the one shown and described with reference to FIG. 1, but there are certain differences.

When the footswitch $F_t$ of the circuit in FIG. 4 is opened after the desired coagulation temperature has been reached (compare the description of the circuit in FIG. 1), then no further regulated current flows into the heating element H at the supply point E, which heating element was preheated with regulated direct current. The preheating current from the section 1 then flows via the diode $D_3$, a resistor $R_3$ and the heating element H when the switch of the voltage source in the section 1 is switched on, which voltage source is regulated to supply a constant voltage of + 5 volts. The resistance of the heating element H still has the high resistance which existed at the moment at which the auxiliary current from the control section was terminated, however, only the preheating current from the voltage source flows in the heating element H at this time. The resistance of the element H decreases slowly to a value at which the preheating current remains constant. This is visible at the instrument TM of the optical indicating means or section 4. In parallel thereto, the voltage at the input of the audible indicating section 6 decreases and this causes the tone frequency of the sound emanating from the loudspeaker to decrease from higher to lower frequencies, that is in accordance with the decrease in temperature the sound emenating from the loudspeaker also decreases in frequency and intensity.

If it is now desired that in the heating phase the beginning of the audible temperature control is to be adjustable, and that in the cooling phase the end of the audible temperature control is to be adjustable, then there are two ways of doing this in the circuit of the device.

According to FIG. 4 a polarized relay PR is provided, which maintains the input of the audible temperature indicator section 6 shorted until upon reaching of a desired temperature in the heating phase of the heating element H the armature NS of the relay PR switches and terminates the shorting of the input of the section 6. The sound generator now begins to operate and produces a sound which increases in frequency as the heating proceeds and increases. The armature NS immediately restores the shorting of the input of the section 6 when during the cooling phase of the heating element H the same temperature is reached which during the heating phase triggered the initiation of the sound. Thus, the sound of decreasing frequency during the cooling phase is terminated when this temperature is reached. The adjustable resistor $R_{11}'$ makes it possible to select any desired starting and terminating temperature.

Figure 5B:
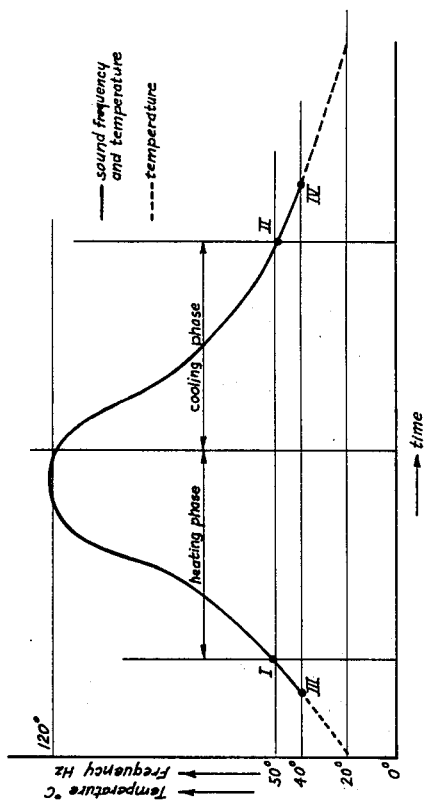
FIG. 5B is a graph illustrating heating and cooling of the heating element and the progress of the audible indication.
Figure 5A:
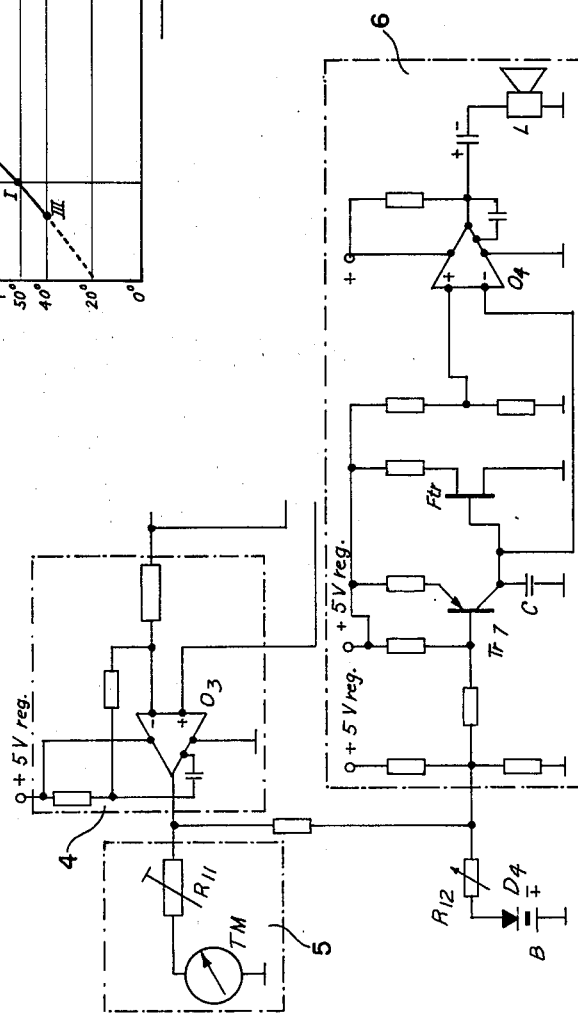
FIG. 5A is a further circuit diagram illustrating another embodiment of the invention.

A further possibility is illustrated in FIG. 5A. According to the circuit in FIG. 5A the polarized relay PR and the adjustable resistor $R_{11}$ have been omitted. In their place, a diode $D_4$ and an adjustable resistor $R_{12}$ are provided which supply the voltage of a battery B as a compensating voltage to the input of the audible indicating section 6. This compensating voltage can be selected with the resistor $R_{12}$ in accordance with the desired starting and terminating temperature. If the voltage derived from the optical temperature indicating section 5 exceeds the preselected compensating voltage, then the tone generator of section 6 begins to operate, and if the voltage is equal to the preselected compensating voltage, then the tone generator ceases to operate. In other words, the beginning of the operation takes place at a preselected temperature below the desired coagulation temperature, and the termination of the operation also takes place at the same preselected temperature below the coagulation temperature.

FIG. 5B is self-explanatory and shows in a right-angle coordinate system the curve indicating temperature and frequency variations, plotted against starting temperatures I and III and terminating temperatures II and IV.

When desired, the time switch 7 can be switched on with the footswitch $F_t$ (via the broken-line conductor) to provide an indication of the end of the heating phase, during the time during which the sound is produced to indicate the heating or cooling phase. The output of the time switch 7 is connected to an electrically operated bell GL, which indicates the end of the heating phase by a onetime operation, i.e. by producing a one-time bell tone when the heating phase is terminated and the cooling phase begins.

It should be understood that the embodiments described and illustrated herein are exemplary and that various modifications will offer themselves to those skilled in the art. Such modifications are intended to be encompassed within the protection sought in the scope of the appended claims.

I claim:
1. A device for causing blood coagulation, particularly for use in endoscopy, comprising
  a support having an end portion;
  an electrically operated thermo-element on said end portion;
  current supplying means for supplying electrical current to said thermo-element to increasingly raise the temperature thereof in a predetermined gradient to a level at which it has a coagulation-causing temperature;
  control means for maintaining said temperature steady when said level is reached;
  visual indicating means for visually indicating the heating of said thermo-element to said level; and
  audible indicating means responsive to the increasing heating of said thermo-element by producing a sound increasing in intensity in correspondence with the increasing heating gradient until said level is reached so as to indicate that the device is ready for use, and which thereafter continues at constant intensity.

2. A device as defined in claim 1, wherein said current supplying means comprises a first current source means for supplying a preheating current, and a second current source means for supplying a temperatureregulating current.

3. A device as defined in claim 2, wherein said first current supplying source means comprises a voltage-regulated source supplying a + 5 volt current.

4. A device as defined in claim 2, wherein said second current source means is a part of said control means and comprises a circuit including a first operational amplifier, transistor means and resistor means in circuit with said amplifier, said control means further comprising a temperature regulator including a second operational amplifier and diode means in circuit with the same.

5. A device as defined in claim 4, wherein said resistor means comprises a first variable resistor in circuit with said thermo-element and which controls the amount of current supplied to said thermo-element, and a second variable resistor also in circuit with said thermo-element and which maintains the current supply to said thermo-element constant when said temperature level is reached.

6. A device as defined in claim 5, wherein said control means is operative for maintaining the potential entering said thermo-element constant when the total current flowing through said thermo-element is also constant.

7. A device as defined in claim 6, wherein said thermo-element is at least in part of Alumel wire.

8. A device as defined in claim 5, said second operational amplifier having a negative pole, and wherein said visual indicating means comprises a temperature-indicating unit, a measuring amplifier connected to said unit and having a negative pole connected with a tap of said second variable resistor and a positive pole connected to said negative pole of said second operational amplifier and to said thermo-element, said second operational amplifier also having a positive pole connected to said tap.

9. A device as defined in claim 8, wherein said measuring amplifier has an output and said audible indicating means has an input connected to said output, said audible indicating means comprising a saw-toothwave generator, a capacitor, a double-base transistor, a third operational amplifier and a loudspeaker, and circuit means connecting said generator, capacitor, transistor and third operational amplifier with one another, the signal entering said input of said audible indicating means being operative to control the operation of said wave generator so that the frequency of the waves generated by the same increases as a function of the increasing temperature of said thermo-element whereby the loudspeaker reproduces a sound of increasing intensity, said signal causing the frequency of waves produced by said wave generator to remain constant once said temperature level is reached whereby the loudspeaker reproduces a sound of constant intensity.

10. A device as defined in claim 9, said audible indicating means further comprising a time switch, a foot-operated switch and a plurality of series-connected monostable multivibrators, and circuit means connecting said switches and multivibrators, activation of said foot-operated switch resulting in generation of an impulse which is supplied to said multivibrators to trigger the same whereupon the input of said audible indicating means is shorted upon expiration of a preselected time to furnish a signal which indicates that said foot-operated switch is to be deactivated.

11. A device as defined in claim 1; further comprising an additional thermo-element; said control means comprising pulse generating means operative for controlling the supply of electrical current to both of said thermo-elements via an opto-coupler connected therewith, said opto-coupler having a photoelectric diode and heating of said thermo-elements being interrupted when identical DC voltages obtain in the circuit at opposite sides of said photoelectric diode; and a variable resistor means for controlling the current supply and thereby the temperature level.

12. A device as defined in claim 11, said control means also including an operational amplifier and a compensator through which current flows to said additional thermo-element, said current flowing through said compensator in the intervals between positive pulses generated by said pulse generating means and serving to indicate via said operational amplifier and said visual indicating means the instaneaneous temperature of the first-mentioned thermo-element.

13. A device as defined in claim 12, said audible indicating means including a three-stage time switch, a loudspeaker and an astable multivibrator serving as a signal generator for said loudspeaker; further comprising a footswitch connected in circuit with said control means and both of said indicating means and operative for activating said pulse generating means, time switch and astable multivibrator.

14. A device as defined in claim 13, wherein said thermo-element is a length of Thermo-Coax conductor having a jacket and a thermo-conductor core surrounded by said jacket, said jacket and core being conductively joined at one end.

15. A device as defined in claim 1, wherein said control means and indicating means comprise component means operative for initiating said sound only when the temperature of said thermo-element reaches a selectively adjustable level below the first-mentioned level, and for decreasing said sound in intensity to zero when the temperature of said thermo-element cools from said first-mentioned level to said selectively adjustable level.

16. A device as defined in claim 15, wherein said audible indicating means comprises polarized relay means operative for shorting the input of audible indicating means until the temperature of said thermo-element exceeds said selectively adjustable level, and for shorting said input again when said temperature of said thermo-element decreases below said selectively adjustable level.

17. A device as defined in claim 16, further comprising variable resistor means for setting said selectively adjustable level relative to the first-mentioned level.

18. A device as defined in claim 15, wherein said audible indicating means comprises a battery, a diode and a variable resistor in circuit with one another and operative for supplying the battery voltage as a compensating voltage to the input of said audible indicating means.

19. A device as defined in claim 15, further comprising a time switch means for timing the heating of said thermo-element, and a footswitch means for activating the operation of all of said means, said audible indicating means further comprising an electrically operated bell, and said time switch means generating at the end of the timed period an output signal which is applied to said bell so as to make the same operate once when the end of the timed heating period is reached.

20. A method of operating a blood-coagulating device, particularly in endoscopy, comprising the steps of
electrically heating a thermo-element which is mounted on a support and is to supply heat to tissue when its temperature reaches a predetermined level;
maintaining the heat of said thermo-element steady when said temperature level is reached;
visually indicating the increasing heatingup of said thermo-element to said temperature level; and
audibly indicating the increasing heatingup by generating a sound which increases in intensity until said temperature level is reached and thereafter remains steady as long as said temperature level remains steady.

21. A method as defined in claim 20, wherein the generation of said sound is initiated only at a selectively adjustable heating level below said temperature predetermined level.

22. A method as defined in claim 21; and further comprising the step of decreasing said sound in intensity when the temperature of said thermo-element decreases below said predetermined level as the element cools.

23. A method as defined in claim 22, wherein the step of decreasing comprises continuously decreasing the intensity of said sound down to zero by the time said selectively adjustable level is reached.

* * * * *